United States Patent [19]

Steck et al.

[11] Patent Number: 5,015,785
[45] Date of Patent: May 14, 1991

[54] PREPARATION OF MIXTURES OF ISOMERIC CRESOLS WITH A MOLAR RATIO OF PARA- TO META-CRESOL OF AT LEAST 0.6:1 TO 10:1

[75] Inventors: Werner Steck; Helmut Lermer, both of Ludwigshafen; Matthias Schwarzmann, Limburgerhof; Toni Dockner, Meckenheim, all of Fed. Rep. of Germany

[73] Assignee: BASF Aktiengesellschaft, Ludwigshafen, Fed. Rep. of Germany

[21] Appl. No.: 564,323

[22] Filed: Aug. 8, 1990

[30] Foreign Application Priority Data

Aug. 9, 1989 [DE] Fed. Rep. of Germany ....... 3926290

[51] Int. Cl.$^5$ .................... C07C 37/48; C07C 37/68; C07C 39/06
[52] U.S. Cl. .................................. 568/783; 568/716; 568/791
[58] Field of Search ...................... 568/716, 783, 791

[56] References Cited

U.S. PATENT DOCUMENTS

| 4,283,571 | 8/1981 | Keim et al. | 568/783 |
| 4,503,269 | 3/1985 | Engel et al. | 568/783 |
| 4,590,306 | 5/1986 | Korff et al. | 568/783 |
| 4,605,790 | 8/1986 | Wojtkowski | 568/783 |
| 4,691,063 | 9/1987 | Engel et al. | 568/783 |
| 4,709,102 | 11/1987 | Gupta | 568/783 |

FOREIGN PATENT DOCUMENTS

| 0122323 | 9/1981 | Japan | 568/783 |
| 2012271 | 7/1979 | United Kingdom | 568/783 |

Primary Examiner—Werren B. Lone
Attorney, Agent, or Firm—John H. Shurtleff

[57] ABSTRACT

A process for the preparation of mixtures of isomeric cresols with a molar ratio of para- to meta-cresol of from 0.6:1 to 10:1 by isomerization of cresol mixtures or ortho- and/or metal-cresol on zeolite catalysts of the pentasil type in the gas phase at from 300° to 600° C. under from 0.01 to 50 bar entails the mean particle size of the zeolite catalyst being at leat 3 μm, and the selectivity in the established test for the disproportionation of ethylbenzene to diethylbenzene isomers being at least 60% for para-diethylbenzene.

10 Claims, No Drawings

PREPARATION OF MIXTURES OF ISOMERIC CRESOLS WITH A MOLAR RATIO OF PARA- TO META-CRESOL OF AT LEAST 0.6:1 TO 10:1

The present invention relates to a process for the isomerization of cresols, in particular o-cresol, on zeolite catalysts to give mixtures of isomers in which the molar ratio of p-cresol to m-cresol is at least 0.6:1.

GB-A-2 012 271 discloses a process for the catalytic isomerization of o-cresol on aluminum silicate zeolites which, in the best case, produces a p/m-cresol molar ratio of 0.41:1.

U.S. Pat. No. 4,503,269 discloses a process for the isomerization of o-cresol to give a mixture of meta- and para-cresol, and the isomerization of m-cresol to pcresol with a little o-cresol on aluminosilicate zeolites in the presence of 1 to 10 mol of hydrogen per mol of cresol. Despite the presence of hydrogen, in the best case the p/m-cresol molar ratio is only 0.35:1 in the product from the process.

U.S. Pat. No. 4,691,063 furthermore discloses a process for the isomerization of cresols on phosphorus-containing aluminosilicate zeolites containing 1 to 8% by weight of phosphorus at from 350° to 500° C. and under 1 to 60 atm. In the best case, the p/m-cresol molar ratio yielded by this process on phosphorus-modified zeolites is 0.46:1.

Accordingly, to date the isomerization of cresols has produced only ternary mixtures of isomers with, in the best case, a p/m-cresol molar ratio of 0.46:1. Thus, after the removal of o-cresol by distillation, there remain binary mixtures with a maximum para/meta-cresol molar ratio likewise of only 0.46:1.

It is easy to see, given the boiling points of 191.1° C. for o-cresol, 202.5° C. for p-cresol and 202.7° C. for m-cresol, why separation of p-cresol and m-cresol by distillation is difficult.

Hence, in order to meet the increasing demand for p-cresol, the object was to prepare, by isomerization of cresol isomers which are available in large quantities, for example the easily obtained o-cresol, or technical cresol, mixtures of isomers with a high content of p-cresol and thus to make the subsequent separation of isomers more economic.

We have accordingly found a process for the preparation of mixtures of isomeric cresols with a molar ratio of para- to meta-cresol of from 0.6:1 to 10:1 by isomerization of cresol mixtures or ortho- and/or meta-cresol on zeolite catalysts of the pentasil type in the gas phase at from 300° to 600° C. under from 0.01 to 50 bar, wherein the mean particle size of the zeolite catalyst is at least 3 μm, and the selectivity in the established test for the disproportionation of ethylbenzene to diethylbenzene isomers is at least 60% for para-diethylbenzene.

The reaction conditions suitable for the isomerization according to the invention are from 300° to 600° C., preferably from 350° to 520° C., under from 0.01 to 50 bar, preferably 0.1 to 5 bar, particularly preferably under atmospheric pressure of about 1 bar. The reaction can be carried out, for example, in the gas phase under atmospheric pressure in a fixed or fluidized bed. Good results can be achieved with a WHSV of 1 to 15 h.: (units of WHSV = g of feed cresol mixture per g of catalyst and hour). It has proven advantageous to carry out this reaction in the presence of inert gases such as nitrogen or noble gases.

We have found that the zeolite crystal size in the catalyst has a large effect on the p-cresol: m-cresol ratio which can be achieved, and that isomeric mixtures which are rich in para-cresol can be obtained, in particular, with crystals whose size is at least about 3 μm, such as from 3 to 500 μm, preferably 20 to 50 μm, particularly preferably 3 to 25 μm or 3 to 15 μm. Determination of the crystal size is straightforward according to the state of the art, either by transmission (TEM) or scanning (SEM) electron microscopy.

A test reaction suitable for characterizing the zeolite catalysts according to the invention is the ethylbenzene disproportionation described in the literature (EBD test, see H.G. Karge, Z. Sarbak, K. Hatada, J. Weitkamp, P.A. Jacobs, J. Catal. 82 (1983) 236).

The test reaction is carried out in a tube reactor with an internal diameter of 6 mm. The stainless steel tube is 90 cm long and is twisted into a spiral. A screen at the end of the reactor prevents the catalyst emerging. The reactor is heated in a hot-air oven. A stream of 10 l (STP) h$^{-1}$ of nitrogen is charged with ethylbenzene in a saturator. The saturator is a jacketed glass tube maintained at 25° C. The inner glass tube of the saturator is packed with a highly porous inert material which is wetted with ethylbenzene. The nitrogen flows upwards and becomes saturated with ethylbenzene in accordance with the partial pressure (1300 Pa at 25° C.) along the packing. The resulting mixture is then passed downwards over the catalyst bed at 250° C. 1 g of catalyst in the form of particles 1 to 2 mm in diameter is employed for this. The discharges from the reactor are condensed and collected for analysis by gas chromatography. It is, of course, possible for the analysis to be automated and take place on-line.

In the first place, the ethylbenzene conversion is a direct measure of the Brönsted acidity of the zeolite. Three isomers of diethylbenzene can be formed, namely o-, m- and p-diethylbenzene. The formation of p-diethylbenzene in turn is used to quantify the para selectivity of the zeolite sample investigated. If the mixture of isomeric diethylbenzenes formed in the EBD test under the stated conditions contains at least 60% p-diethylbenzene, the catalyst is highly suitable for the cresol isomerization according to the invention to give a mixture of isomers rich in para-cresol, which is a feature of the catalysts according to the invention. The discharge from the test reaction often contains only ethylbenzene, benzene and the diethylbenzenes, and the analysis of these by gas chromatography is straight-forward.

The pentasil-type zeolites suitable for the process according to the invention have as secondary structural unit (=secondary building unit, basic unit of the zeolite structure) a five-membered ring composed of $TO_4$ tetrahedrons, possible T cations being Si, Al and Ga. The pentasil zeolites are defined by G. T. Kokotailo and W. M. Meier, Chem. Soc. Spec. Publ. 33 (1980) 133–139. Pentasil zeolites have a high $SiO_2/Al_2O_3$ molar ratio also called modulus—and have pore sizes between those of type A and of type X or Y zeolites. Pentasil zeolites with $SiO_2/Al_2O_3$ ratios of from 25 to 700, for example, have proven very suitable for the process according to the invention. The preparation of these pentasil zeolites is described, inter alia, in U.S. Pat. No. 3,702,886 (ZSM-5), U.S. Pat. No. 3,709,979 (ZSM-11) and U.S. Pat. No. 4,061,724 (Silicalite ®). The isotactic pentasil zeolites disclosed in EP-A-0,034,727 also belong with these.

The aluminosilicate zeolite is prepared, for example, from an aluminum compound, preferably $Al(OH)_3$ or Al$_2$(SO$_4$)$_3$, and a silicon component such as highly disperse silica, silica gel or silica sol, in aqueous amine solution, in particular in polyamines such as 1,6-diaminohexane or 1,3-diaminopropane or triethylenetetramine solution with or without addition of alkali metal or alkaline earth metal, at from 100° to 220° C. under autogenous pressure. The resulting aluminosilicate zeolites have an SiO$_2$/Al$_2$O$_3$ ratio of from 25 to 700, depending on the chosen amounts of starting materials.

Also suitable are gallium silicate zeolites or zeolites which contain both gallium and aluminum as trivalent lattice ion.

Suitable catalysts ar also obtained by preparing, in a first step according to the state of the art, zeolites with large crystals, which do not have sufficient catalytic activity, and then activating the latter, sufficient for the isomerization, by replacing the silicon by aluminum or gallium. Thus it is possible to prepare, for example, virtually aluminum-free zeolites by the method of U.S. Pat. No. 3,702,886 or boron zeolites by the method of EP-A-7 081 or U.S. Pat. No. 4,268,420 in the form of sufficiently large crystals and subsequently to aluminate them according to the state of the art. The alumination can be carried out either in the gas phase at elevated temperature with AlCl$_3$ (M. W. Anderson et al., J. Chem. Soc., Chem. Commun. (1984) 157) or in liquid phase either under atmospheric pressure at up to 100° C. or under autogenous pressure at up to 180° C. Compounds of aluminum which can be used are its salts such as chlorides or nitrates in the form of aqueous solutions. The pH can be in the range from 2.5 to 13. If aluminum is inserted into the lattice in an alkaline medium, it is also possible to use aqueous solutions of KAlO$_2$ or NaAlO$_2$ as sources of aluminum (X. Liu et al., J. Chem. Soc., Chem. Commun. (1986) 582). The pentasil zeolites can be employed for this activation as powders or, after a suitable binder has been burnt off, as extrudates or pellets.

Suitable pentasil zeolites can also be obtained by removing part of the aluminum from the lattice, or replacing it by silicon, in catalysts which are too acidic. This can be carried out by the known hydrothermal methods in the presence of steam, usually followed by treatment with an acid, by extracting with complexing agents such as EDTA or by treatment with SiCl$_4$ at elevated temperature in the gas phase. A more novel method is treatment of the zeolites with an aqueous solution of (NH$_4$)$_2$SiF$_6$ (D. W. Breck, G. W. Skeels, A. C. S., Symp. Ser., 218 (1983); EP-A-0 082 211). Similarly, the surface acidity of the zeolites can be abolished or greatly reduced by calcination in the presence of alkali metal ions.

The zeolite powders resulting after their synthesis, isolation, drying at from 100° to 160° C. and calcination at from 400° to 550° C. can be shaped with a binder in the ratio by mass of zeolite to binder of from 90:10 to 40:60 into, for example, extrudates or pellets Suitable binders are, inter alia, various silicas such as highly disperse SiO$_2$, various aluminas such as boehmite, mixtures of SiO$_2$ and Al$_2$O$_3$ or clay, amorphous aluminosilicates or TiO$_2$. After the extrudates or pellets have been shaped they are dried at 110° C. and calcined at around 500° C.

Very suitable catalysts are also obtained when the isolated zeolite is shaped immediately after drying and subjected to calcination only after shaping. The pentasil zeolites can be employed in pure form, without binder, as extrudates or pellets, examples of extrusion or peptization agents which can be used being ethylcellulose, stearic acid, potato starch, formic acid, oxalic acid, acetic acid, nitric acid, ammonia, amines and graphite or mixtures thereof.

If, by reason of the mode of its preparation, before the application of the zeolite it is not in the catalytically active, acidic H form but, for example, in the Na form, the latter can be converted completely or partially into the desired H form by ion exchange, eg. with ammonium ions, and subsequent calcination or by treatment with acids.

If inactivation caused by deposition of carbon occurs when the zeolite catalysts are used according to the invention, it is advisable to regenerate the zeolites by burning off the carbon with air or with an air/N$_2$ mixture at from 400° to 550° C. This usually returns the zeolites to their initial activity.

It may be advantageous, in order to achieve maximum selectivity, high conversion and long useful lives, to modify the zeolites in such a way that the content of modifying elements ensures adequate activity of the catalysts.

An example of suitable modification of the catalysts is to dope the shaped or unshaped zeolites with metal salts by ion exchange or impregnation. Examples of metals which are used are noble metals such as Pd or Pt.

The doping is expediently carried out in such a way that, for example, the shaped zeolite is placed in an ascending tube and, for example, an aqueous or ammoniacal solution of a halide or nitrate of the metals described above is passed over it at from 20° to 100° C. Ion exchange. of this type can be applied, for example, to the hydrogen, ammonium or alkali metal form of the zeolite. Another way of applying metal to the zeolite is to impregnate it, for example, with a halide, a nitrate, a carbonate or an oxide of the metals described above in aqueous, alcoholic or ammoniacal solution. Both ion exchange and impregnation will be followed by at least one drying, and possibly another calcination.

The catalysts described below can be employed as 2- to 4-mm extrudates or as pellets of diameter 3 to 5 mm or as particles of from 0.1 to 0.5 mm in size or as material in a fluidized bed.

Cresols are important intermediates for the preparation of perfumes and crop protection agents. There is particular interest in para-cresol which is required, for example, for the preparation of antioxidants (cf. Ullmanns Encyklopädie der technischen Chemie, 4th Ed., vol. 15, p. 72, Verlag Chemie, Weinheim, 1978).

EXAMPLES

Isomerization of cresols

EXAMPLES 1 TO 22 AND COMPARATIVE EXAMPLES V 1 TO V 4

Gas-phase reactions for the isomerization of o-cresol

The gas-phase reactions were carried out under isothermal conditions and under atmospheric pressure in a tube reactor (spiral, 0.6 cm internal diameter, tube length 90 cm) with a single passage through a fixed bed catalyst at from 250° to 500° C. The weight of catalyst was from 2 to 20 g. The reaction products were analyzed by gas chromatography.

To prepare mixtures of isomeric cresols in the tube reactor described above, the starting materials, e.g. o-cresol, were fed into the reactor continuously under atmospheric pressure by a metering pump and then passed in the form of a gas, with a stream of carrier gas of, for example, from 5 to 30 liters (STP)/h nitrogen, over the catalyst. The gaseous precursors and reaction products are passed either in the ascending or descending mode through the fixed bed catalyst.

After the isomerication is complete, the discharge from the reactor is condensed and analyzed by gas chromatography after the running time stated in hours [h]. The conversions (C) and selectivities (S) are indicated in the Tables in percentage areas.

TABLE 1

Isomerization of o-cresol
Isomerization of o-cresol with 4 g of catalyst; $N_2$ (l/h) = nitrogen flow rate in liters (STP)/h; SM = starting material o-cresol in ml/h. C (6 h) = o-cresol conversion after 6 hours; p/m (6 h) = ratio of p-cresol to m-cresol in the product discharged after 6 hours; S(c) = selectivity for p-cresol + m-cresol as a measure of the selectivity for the isomeric cresols which can be isolated or of the loss of o-cresol to byproducts.

| Example | T °C. | $N_2$ l/h | SM | C (6 h) | p/m (6 h) | S(c) p + m% | Catalyst No. |
|---|---|---|---|---|---|---|---|
| 1 | 450 | 10 | 10 | 37.9 | 0.60 | 61.2 | 1 |
| 2 | 250 | 10 | 10 | 1.3 | 0.88 | 57.0 | 2 |
| 3 | 350 | — | — | 10.9 | 0.99 | 78.8 | 2 |
| 4 | 450 | — | — | 11.8 | 0.88 | 79.4 | 2 |
| 5 | 450 | — | 20 | 11.9 | 0.81 | 92.8 | 2 |
| 6 | 450 | — | 10 | 15.5 | 0.71 | 85.7 | 2 |
| 7 | — | 10 | — | 7.5 | 1.20 | 90.5 | 2 |
| 8 | — | — | — | 14.6 | 0.67 | 95.5 | 2A |
| 9 | — | — | — | 11.8 | 0.72 | 95.6 | 2B |
| 10 | — | — | — | 8.5 | 1.15 | 89.2 | 2C |
| 11 | — | — | — | 8.8 | 1.06 | 87.9 | 2D |
| 12 | 450 | 10 | 10 | 13.1 | 0.81 | 95.2 | 3 |
| 13 | — | 10 | 10 | 4.0 | 0.72 | 83.9 | 4 |
| 14 | — | 10 | 10 | 18.7 | 0.60 | 97.5 | 5A |
| 15 | — | — | — | 16.3 | 0.64 | 96.7 | 5B |
| 16 | 350 | 10 | 10 | 5.0 | 0.67 | 80.4 | 6 |
| 17 | 450 | — | 10 | 16.0 | 0.98 | 93.9 | 6 |
| 18 | 450 | — | 20 | 7.6 | 1.38 | 100 | 6 |
| 19 | 500 | — | 20 | 10.2 | 1.54 | 94.4 | 6 |
| 20 | 450 | — | 30 | 7.6 | 1.36 | 99.8 | 6 |
| 21 | 450 | 10 | 10 | 7.3 | 0.70 | 84.5 | 7A |
| 22 | — | — | — | 5.2 | 0.65 | 87.6 | 7B |
| V1 | 450 | 10 | 10 | 53.6 | 0.34 | 96.8 | 8 |
| V2 | — | — | — | 65.1 | 0.34 | 76.0 | 9 |
| V3 | — | — | — | 6.4 | 0.09 | 47.6 | 10 |
| V4 | — | — | — | 20.3 | 0.23 | 12.7 | 11 |
| Thermodyn. equilibrium | 450 | — | — | — | 0.10 | — | — |

TABLE 2

| Catalyst No. | Crystal size (μm) | % p-DEB in the test of H.G. Karge | Binder | Modification | Modulus |
|---|---|---|---|---|---|
| 1 | 4.0 | 61 | Pseudoboehmite | | 36 |
| 2 | 8.5 | 88 | None | | 42 |
| 2 | 8.5 | 87 | None | | 42 |
| 2A | | 60 | | (*) | 36 |
| 2B | | 92 | | (*) | |
| 2C | | 74 | $SiO_2$ | (*) | |
| 2D | | 64 | SiO | (*) | |
| 3 | 3.0 | 71 | None | 2.4% Pd | 45 |
| 4 | 11.0 | 68 | None | | 51 |
| 5A | 3.0 | 84 | None | | 150 |
| 5B | | 93 | $SiO_2$ | | |
| 6 | 9.0 | 95 | $SiO_2$ | | 154 |
| 7A | 3.5 | 83 | None | | 554 |
| 7B | | 97 | $SiO_2$ | | |
| 8 | 0.2 | 34 | None | | 38.2 |
| 9 | 0.3 | 35 | None | | 72 |
| 10 | — | 40 | $SiO_2$ pure | | |
| 11 | — | 35 | $Al_2O_3$ pure | | |
| | | 28 | Thermodynamic equilibrium at 250° C. | | |

(*) Modification with $(NH_4)_2SiF_6$
Modulus: $SiO_2:Al_2O_3$ molar ratio
p-DEB: para-diethylbenzene

PREPARATION OF THE CATALYSTS

Catalyst 1

An aluminisilicate zeolite of the pentasil type is prepared under hydrothermal conditions and autogenous pressure at 150° from 650 g of highly disperse $SiO_2$, 203 g of $Al_2(SO_4)_3 \times H_2O$ in a mixture of 2.0 kg of water and 9.6 kg of an aqueous solution of 1,6-diaminohexane (50% by weight amine) in a stirred autoclave. The crystalline reaction product is filtered off and washed and then dried at 110° C. for 24 h and calcined at 500° C. for 24 h. This aluminosilicate zeolite contains 80.4% by weight of $SiO_2$ and 3.8% by weight $Al_2O_3$. The crystal size is 4 μm.

This material is shaped together with pseudoboehmite (9 parts of zeolite to 1 part of pseudoboehmite) into 2 mm extrudates which are dried at 110° C. for 16 h and calcined at 500° C. for 16 h.

Catalysts 2, 2A, 2B, 2C and 2D

An aluminosilicate zeolite of the pentasil type is prepared under hydrothermal conditions and autogenous pressure at 184° C. from 700 g of highly disperse $SiO_2$ and 996 g of $Al_2(SO_4)_3 \times 18\ H_2O$ in 12.2 kg of an aqueous solution of triethylenetetramine (38% by weight amine) in a stirred autoclave. The crystalline reaction product is filtered off and washed and then dried at 110° C. for 24 h and calcined at 500° C. for 24 h. This aluminosilicate zeolite contains 92.9% by weight $SiO_2$ and 3.8% by weight $Al_2O_3$; modulus 42. The crystal size is 8.5 μm.

This material is used to prepare, by shaping with a shapingauxiliary, 2 mm extrudates which are dried at 110° C. for 16 h and calcined at 500° C. for 16 h (catalyst 2).

Catalysts 2 A and 2 B : catalyst 2 treated with $(NH_4)_2SiF_6$ and dried at 110° C. (catalyst 2 A) or additionally calcined at 500° C. in the presence of air for 4 hours (catalyst 2 B).

30 g of catalyst 2 are suspended in 125 ml of water in a plastic container. Then 167 ml of an aqueous solution which contains 29.8 g of the hexafluorosilicate are added. The container was closed and heated at 80° C. for 5 hours. The solid was then filtered off and thoroughly washed with hot water (80° C.). The filter cake was dried at 110° C. and then a portion of the zeolite was separated off as catalyst 2 A. The remainder was calcined at 500° C. in the air for 4 hours (catalyst 2 B).

Extrusion of Untreated Catalyst 2 Powder with $SiO_2$

Catalyst 2 powder is shaped with pyrogenic silica (8 parts of zeolite to 2 parts of pyrogenic silica) into 2 mm extrudates which are dried at 130° C. and calcined at 500° C. for 16 h. The extrudates are treated like catalysts 2 A and 2 B with hexafluorosilicate, resulting in catalysts 2 C (dried at 110° C.) and 2 D (additionally calcined).

Catalyst 3

An aluminosilicate zeolite of the pentasil type is prepared under hydrothermal conditions and autogenous pressure at 150° C. for 85 h and then at 160° C. for 85 h from 650 g of highly disperse $SiO_2$, 203 g of $Al_2(SO_4)_3 \times 18\ H_2O$ in a mixture of 1.7 kg of water and 9.6 kg of an aqueous solution of 1,6-diaminohexane (50% by weight amine) in a stirred autoclave. The crystalline reaction product is filtered off and washed and then dried at 110° C. for 24 h and calcined at 500° C. for 24 h. This aluminosilicate zeolite contains 81.4% by weight $SiO_2$ and 3.0% by weight $Al_2O_3$. The crystal size is 3 μm.

This material is used to prepare, by shaping with a shaping auxiliary, 2 mm extrudates which are dried at 110° C. for 16 h and calcined at 500° C. for 16 h.

The extrudates are impregnated with an aqueous $Pd(NO_3)_2$ solution, dried at 130° C. and calcined at 540° C. The Pd content is 2.4% by mass.

Catalyst 4

A commercial ZSM-5 catalyst (2 mm extrudates) in the H form with the following properties was employed:

| Catalyst | $SiO_2/Al_2O_3$ | Crystallite size (μm) |
|---|---|---|
| 4 | 52 | 11 |

Catalyst 5 A

An aluminosilicate zeolite of the ZSM-5 type is prepared under hydrothermal conditions and autogenous pressure at 160° C. from 1.5 kg of pyrogenic silica, 84.0 g of aluminum sulfate 18-hydrate, 0.24 kg of sodium hydroxide, 0.98 kg of tetra-n-propylammonium bromide and 18.0 kg of water in a stirred autoclave. The crystalline reaction product is filtered off and washed and then dried at 110° C. for 24 h and calcined at 500° C. for 24 h. This zeolite has the following composition: 85.4% by weight $SiO_2$, 1.00% by weight $Al_2O_3$, 0.75% by weight Na. The crystal size is 3 μm.

This zeolite is used to prepare, by shaping with a shaping auxiliary, 2 mm extrudates which are dried at 110° C. for 16 h and calcined at 500° C. for 16 h.

The extrudates are subjected to four exchanges with 20% by weight $NH_4Cl$ solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.015% by weight.

Catalyst 5 B

Catalyst 5 B is prepared by shaping the ZSM-5 zeolite from catalyst 5 A with pyrogenic silica in the ratio 8:2 by mass to give 2 mm extrudates which are dried at 110° C. and calcined at 500° C. for 16 h.

The extrudates are subjected to four exchanges with 20% by weight NH Cl solution (15 ml of solution per g of shaped articles) at 80° C. in an ascending tube. They are subsequently washed free of chloride. The extrudates are dried at 110° C. for 10 h and then calcined at 500° C. for 5 h. The Na content is then 0.012% by weight.

Catalyst 6

An aluminosilicate zeolite of the ZSM-5 type is prepared under hydrothermal conditions and autogenous pressure at 160° C. from 150 g of pyrogenic silica, 8.4 g of aluminum sulfate 18-hydrate, 24 g of sodium hydroxide, 98 g of tetra-n-propylammonium bromide and 1.8 kg of water in an autoclave. The crystalline reaction product is filtered off and washed and then dried at 110° C. for 24 h and then calcined at 500° C. for 24 h. This zeolite has the following composition: 86.2% by weight $SiO_2$, 0.95% by weight $Al_2O_3$, 0.67% by weight of Na. The crystal size is 9 μm. The zeolite powder is suspended by stirring with 20% by weight $NH_4Cl$ solution (15 ml of solution per g of zeolite) at 80° C. four times. It is then washed free of chloride. The material is dried at 110° C. and then calcined at 500° C. for 5 h. The Na content is then 0.01% by weight. This zeolite is used to prepare, by shaping with pyrogenic silica (9 parts of zeolite to 1 part of silica), 2 mm extrudates which are dried at 110° C. and calcined at 500° C. for 16 h.

Catalyst 7 A

An aluminosilicate zeolite of the ZSM-5 type is prepared under hydrothermal conditions and autogenous pressure at 160° C. from 1.5 kg of pyrogenic silica, 34.0 g of aluminum sulfate 18-hydrate, 0.22 kg of sodium hydroxide, 1.0 kg of tetra-n-propylammonium bromide and 18.0 kg of water in a stirred autoclave. The crystalline reaction product is filtered off and washed and then dried at 110° C. for 24 h and calcined at 500° C. for 24 h. The zeolite has the following composition: 81.6% by weight $SiO_2$, 0.25% by weight $Al_2O_3$, 0.65% by weight Na. The crystal size is 4 μm.

This zeolite is used to prepare, by shaping with a shaping auxiliary, 2 mm extrudates which are dried at 110° C. for 16 h and calcined at 500° C. for 16 h.

The extrudates are subjected to four exchanges with 20% by weight $NH_4Cl$ solution (15 ml of solution per g of shaped article) at 80° C. in an ascending tube. They are then washed free of chloride. The extrudates are dried at 110° C. for 10 h and then calcined at 500° C. for 5 h. The Na content is then 0.17% by weight.

Catalyst 7 B

Catalyst 7 B is prepared by shaping the ZSM-5 zeolite from catalyst 7 A with pyrogenic silica in the ratio 8:2 by mass into 2 mm extrudates which are dried at 110° C. and calcined at 500° C. for 16 h.

The extrudates are subjected to four exchanges with 20% by weight $NH_4Cl$ solution (15 ml of solution per g of shaped articles) at 80° C. in an ascending tube. They are then washed free of chloride. The extrudates are dried at 110° C. for 10 h and then calcined at 500° C. for 5 h. The Na content is then 0.15% by weight.

Catalyst 8 (Comparative catalyst)

An aluminosilicate zeolite of the ZSM-11 type is prepared under hydrothermal conditions and autogenous pressure at 160° C. from 10.9 kg of water, 6.3 kg of sodium waterglass (8.0% by weight $Na_2O$, 26.5% by weight $SiO_2$), 180 g of aluminum sulfate 18-hydrate, 600 g of conc. sulfuric acid and 600 q of 1,8-diaminooctane in a stirred autoclave. The crystalline reaction product is filtered off and washed and then dried at 110° C. for 24h and calcined at 500° C. for 24h. This zeolite has the following composition: 81.8% by weight $SiO_2$, 1.82% by weight $Al_2O_3$. The crystal size is 0.2μm.

This material is used to prepare, by shaping with a shaping auxiliary, 2 mm extrudates which are dried at 110° C. for 16h and calcined at 500° C. for 16h.

The extrudates are subjected to four exchanges with 20% by weight NH$_4$Cl solution (15 ml of solution per g of shaped articles) at 80° C. in an ascending tube. They are then washed free of chloride. The extrudates are dried at 110° C. for 10 h and then calcined at 500° C. for 5 h. The Na content is then 0.015% by weight.

Catalyst 9 (Comparative catalyst)

An aluminosilicate zeolite of the pentasil type is prepared under hydrothermal conditions and autogenous pressure at 150° C. from 650 g of highly disperse SiO$_2$, 203 g of Al$_2$(SO$_4$)$_3 \times$ 18 H$_2$O in 11.3 kg of an aqueous solution of 1,6-diaminohexane (42% by weight amine) in a stirred autoclave. The crystalline reaction product is filtered off and washed and then dried at 110° C. for 24 h and calcined at 500° C. for 24 h. This aluminosilicate zeolite contains 92.6% by weight SiO$_2$ and 4.6% by weight Al$_2$O$_3$; modulus 38. The crystal size is 0.3 μm.

This material is used to prepare, by shaping with a shaping auxiliary, 2 mm extrudates which are dried at 110° C. for 16 h and calcined at 500° C. for 16 h.

Catalyst 10 (Comparative catalyst) is a commercial Al$_2$O$_3$ (D 10-10 ®).

Catalyst 11 (Comparative catalyst) is a commercial SiO$_2$ (D 11-10 ®).

We claim:

1. A process for the preparation of mixtures of isomeric cresols with a molar ratio of para- to metacresol of from 0.6:1 to 10:1 by isomerization of cresol mixtures or ortho- and/or meta-cresol on zeolite catalysts of the pentasil type in the gas phase at from 300 to 600° C. under from 0.01 to 50 bar, wherein the mean particle size of the zeolite catalyst is at least 3 μm, and the selectivity in the established test for the disproportionation of ethylbenzene to diethylbenzene isomers is at least 60% for para-diethylbenzene.

2. A process as claimed in claim 1, wherein mixtures of isomers with a molar ratio of para- to meta-cresol of from 0.6:1 to 3:1 are obtained.

3. A process as claimed in claim 1, wherein zeolites with a mean particle size of from 3 to 500 μm are used.

4. A process as claimed in claim 1, wherein zeolites with a mean particle size of from 3 to 50 μm are used.

5. A process as claimed in claim 1, wherein zeolites with a mean particle size of from 3 to 25 μm are used.

6. A process as claimed in claim 1, wherein zeolites with a mean particle size of from 3 to 15 μm are used.

7. A process as claimed in claim 1, wherein aluminosilicate zeolites or gallium silicate zeolites of the pentasil type are used as zeolite catalysts.

8. A process as claimed in claim 1, wherein zeolites of the pentasil type which are doped with palladium and/or platinum are used.

9. A process as claimed in claim 1, wherein o-cresol is employed for the isomerization.

10. A process as claimed in claim 1, wherein the isomerization is carried out in the gas phase at from 350° to 520° C.

* * * * *

UNITED STATES PATENT AND TRADEMARK OFFICE
CERTIFICATE OF CORRECTION

PATENT NO. : 5,015,785
DATED : May 14, 1991
INVENTOR(S) : Steck et al

It is certified that error appears in the above-identified patent and that said Letters Patent is hereby corrected as shown below:

Title Page:

In the Abstract:

At line 4, please change "metal-cresol" to read --meta-cresol--.

Signed and Sealed this

Seventeenth Day of November, 1992

Attest:

DOUGLAS B. COMER

*Attesting Officer*     *Acting Commissioner of Patents and Trademarks*